United States Patent
Liu et al.

(10) Patent No.: US 10,729,337 B2
(45) Date of Patent: Aug. 4, 2020

(54) DEVICE AND METHOD FOR NON-INVASIVE LEFT VENTRICULAR END DIASTOLIC PRESSURE (LVEDP) MEASUREMENT

(71) Applicants: The Johns Hopkins University, Baltimore, MD (US); Boston Scientific Scimed Inc., Maple Grove, MN (US)

(72) Inventors: Qian Liu, Toronto (CA); Nichaluk Leartprapun, Ithaca, NY (US); Jackline Wanjala, San Francisco, CA (US); Soumyadipta Acharya, Baltimore, MD (US); Andrew Bicek, Elk River, MN (US); Viachaslau Barodka, Baltimore, MD (US); Umang Anand, Plymouth, MN (US); Majd Alghatrif, Baltimore, MD (US); David Kass, Baltimore, MD (US); B. Westbrook Bernier, Miami, FL (US); Chao-Wei Hwang, West Friendship, MD (US); Peter Johnston, Baltimore, MD (US); Trent Langston, Costa Mesa, CA (US)

(73) Assignees: The Johns Hopkins University, Baltimore, MD (US); Boston Scientific Scimed Inc., Maple Grove, MN (US)

( * ) Notice: Subject to any disclaimer, the term of this patent is extended or adjusted under 35 U.S.C. 154(b) by 190 days.

(21) Appl. No.: 15/571,771
(22) PCT Filed: May 5, 2016
(86) PCT No.: PCT/US2016/031041
§ 371 (c)(1),
(2) Date: Nov. 3, 2017
(87) PCT Pub. No.: WO2016/179425
PCT Pub. Date: Nov. 10, 2016

(65) Prior Publication Data
US 2018/0160917 A1 Jun. 14, 2018

Related U.S. Application Data
(60) Provisional application No. 62/156,998, filed on May 5, 2015.

(51) Int. Cl.
*A61B 5/021* (2006.01)
*A61B 5/00* (2006.01)
(Continued)

(52) U.S. Cl.
CPC ...... *A61B 5/02108* (2013.01); *A61B 5/02141* (2013.01); *A61B 5/0535* (2013.01);
(Continued)

(58) Field of Classification Search
CPC . A61B 5/02108; A61B 5/0535; A61B 5/7267; A61B 5/02141; A61B 5/0452; A61B 5/1455; A61B 5/14551
See application file for complete search history.

(56) References Cited

U.S. PATENT DOCUMENTS 4,203,451 A * 5/1980 Panico .............. A61B 5/022
600/485
2004/0220637 A1* 11/2004 Zdeblick ............ A61B 5/02028
607/17

(Continued)

FOREIGN PATENT DOCUMENTS

JP 2003-501194 A 1/2003

OTHER PUBLICATIONS

Abd-El-Aziz, "Noninvasive prediction of left ventricular end-diastolic pressure in patients with coronary artery disease and preserved ejection fraction", Canadian Journal of Cardiology, vol. 28, Issue 1, Jan.-Feb. 2012, pp. 80-86 (Year: 2012).*
(Continued)

Primary Examiner — Eric F Winakur
Assistant Examiner — Chu Chuan Liu
(74) Attorney, Agent, or Firm — Venable LLP; Henry J. Daley; Miguel A. Lopez

(57) ABSTRACT

The present application relates to systems and methods for non-invasively determining at least one of left ventricular
(Continued)

$$LVEDP = DBP - \int_0^{IVCT} \frac{dP_{LV}(t)}{dt} dt$$

☐ DBP - Diastolic blood pressure
☐ IVCT - Isovolumetric Contraction Time
☐ dP/dt - Rate Of Pressure Rise In Lv Due To Contraction end diastolic pressure (LVEDP) or pulmonary capillary wedge pressure (PCWP) in a subject's heart, comprising: receiving, by a computer, a plurality of signals from a plurality of non-invasive sensors that measure a plurality of physiological effects that are correlated with functioning of said subject's heart, said plurality of physiological effects including at least one signal correlated with left ventricular blood pressure and at least one signal correlated with timing of heartbeat cycles of said subject's heart; training a machine learning model on said computer using said plurality of signals for periods of time in which said plurality of signals were being generated during a heart failure event of said subject's heart; determining said LVEDP or PCWP using said machine learning model at a time subsequent to said training and subsequent to said heart failure event.

23 Claims, 14 Drawing Sheets

(51) Int. Cl.
*A61B 5/053* (2006.01)
*A61B 5/0452* (2006.01)
(52) U.S. Cl.
CPC .......... *A61B 5/7267* (2013.01); *A61B 5/0452* (2013.01); *A61B 2562/0204* (2013.01)

(56) References Cited

U.S. PATENT DOCUMENTS

| | | |
|---|---|---|
| 2005/0043767 A1 | 2/2005 | Belalcazar |
| 2009/0118627 A1 | 5/2009 | Stahmann et al. |
| 2010/0228140 A1 | 9/2010 | Hirsh |
| 2014/0155764 A1 | 6/2014 | Silber |

OTHER PUBLICATIONS

International Search Report and Written Opinion in International Patent Application No. PCT/US2016/031041, dated Aug. 16, 2016.
Martin et al, "Direct Correlation of External Systolic Time Intervals with Internal Indices of Left Ventricular Function in Man." Circulation, 44: 419-431 (1971).
Chen et al., "Estimation of Central Aortic Pressure Waveform by Mathematical Transformation of Radial Tonometry Pressure Validation of Generalized Transfer Function," Circulation, 95: 1827-1836 (1997).
Kips et al., "Comparison of central pressure estimates obtained from SphygmoCor, Omron HEM-9000AI and carotid applanation tonometry," J. Hypertens., 29(6): 1115-1120 (2011).

* cited by examiner

DEVICE AND METHOD FOR NON-INVASIVE LEFT VENTRICULAR END DIASTOLIC PRESSURE (LVEDP) MEASUREMENT

CROSS-REFERENCE OF RELATED APPLICATION

This application is a U.S. National Stage Application under 35 U.S.C. § 371 of PCT/US2016/031041, filed May 5, 2016, which claims the benefit of U.S. Provisional Application No. 62/156,998, filed on May 5, 2015, the entire contents of each of which are hereby incorporated by reference.

BACKGROUND

1. Technical Field

The field of the currently claimed embodiments of this invention relates to methods and systems for non-invasively determining left ventricular end diastolic pressure (LVEDP) and/or pulmonary capillary wedge pressure (PCWP).

2. Discussion of Related Art

Successful heart failure management, both in and out of the hospital, depends on intimate knowledge and tracking of cardiac pressures that inform the fluid status of patients. The most important of these pressures is left ventricular end diastolic pressure (LVEDP). Both physicians and surgeons rely heavily on the cardiac chamber pressures, especially that in the left ventricle, to assess the fluid volume status of patients and heart function pre and post procedures in the in-hospital setting, outpatient clinics or when patients are at their home.

However, current methodologies of assessing left ventricular end diastolic pressure are either invasive in nature with associated complications or non-suitability for specific patient types, or they allow only measurement of surrogate parameters in lieu of LVEDP. Examples of invasive methods include invasive catheterization procedures that are inaccessible for regular use or are contraindicated for a large subset of the heart failure population. Other non-invasive methods of quantifying LVEDP do so by obtaining surrogate pressures. Thus there is a compelling need for a means of measuring LVEDP accurately, safely and noninvasively.

SUMMARY

Some embodiments of the instant invention are directed to a system for non-invasively determining at least one of left ventricular end diastolic pressure (LVEDP) or pulmonary capillary wedge pressure (PCWP) in a subject's heart, comprising: a signal processor; a pressure sensor operatively connected to said signal processor to communicate therewith; and a timing sensor operatively connected to said signal processor to communicate therewith, wherein said pressure sensor is structured to be brought into mechanical connection with an external surface region of said subject so as to provide peripheral pressure signals corresponding to a peripheral artery blood pressure, wherein said timing sensor is structured to non-invasively measure a physical property of said subject's heart that is correlated with said subject's heart beat so as to provide timing signals comprising timing information with respect to heartbeat cycles, and wherein said signal processor is configured to receive said peripheral pressure signals and said timing signals and to non-invasively determine an estimated value of said subject's LVEDP or PCWP based at least partially thereon.

Some embodiments of the instant invention are directed to a computer-implemented method for non-invasively determining at least one of left ventricular end diastolic pressure (LVEDP) or pulmonary capillary wedge pressure (PCWP) in a subject's heart, comprising: receiving, by a computer, a plurality of signals from a plurality of non-invasive sensors that measure a plurality of physiological effects that are correlated with functioning of said subject's heart, said plurality of physiological effects including at least one signal correlated with left ventricular blood pressure and at least one signal correlated with timing of heartbeat cycles of said subject's heart; training a machine learning model on said computer using said plurality of signals for periods of time in which said plurality of signals were being generated during a heart failure event of said subject's heart; determining said LVEDP or PCWP using said machine learning model at a time subsequent to said training and subsequent to said heart failure event.

Some embodiments of the instant invention are directed to a computer-readable medium comprising computer-executable code for non-invasively determining at least one of left ventricular end diastolic pressure (LVEDP) or pulmonary capillary wedge pressure (PCWP) in a subject's heart, said computer-readable medium, when executed by said computer causes said computer to: receive a plurality of signals from a plurality of non-invasive sensors that measure a plurality of physiological effects that are correlated with functioning of said subject's heart, said plurality of physiological effects including at least one signal correlated with left ventricular blood pressure and at least one signal correlated with timing of heartbeat cycles of said subject's heart; train a machine learning model on said computer using said plurality of signals for periods of time in which said plurality of signals were being generated during a heart failure event of said subject's heart; determine said LVEDP or PCWP using said machine learning model at a time subsequent to said training and subsequent to said heart failure event.

BRIEF DESCRIPTION OF THE DRAWINGS

Further objectives and advantages will become apparent from a consideration of the description, drawings, and examples.

DETAILED DESCRIPTION

Figure 1:
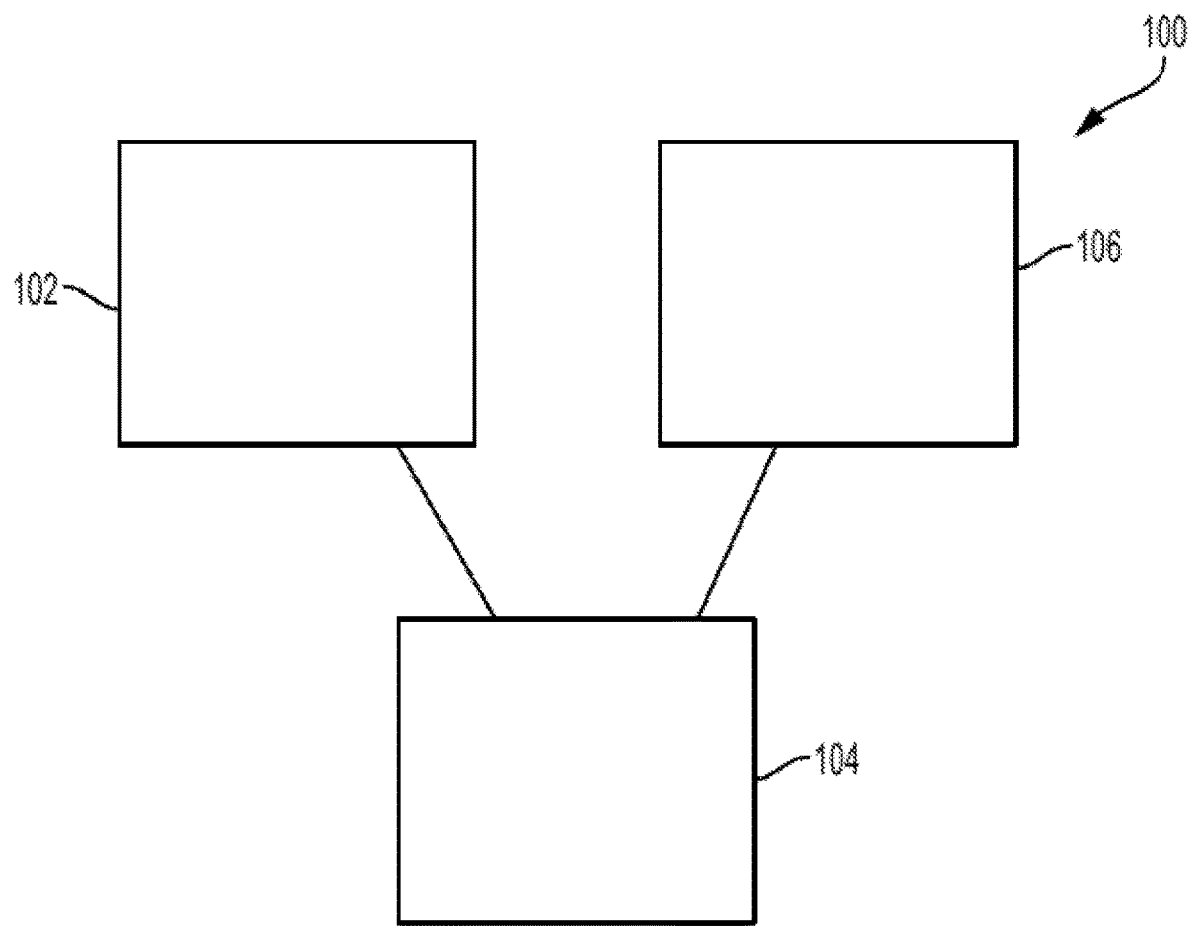
FIG. 1 shows a schematic of an embodiment of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "signal processor" is intended to refer to a device capable of processing the signals of interest. It could be a hard-wired device such as, but not limited to, an ASIC or an FPGA, or it could be a programmable device. In some embodiments, the signal processor can be one or more microprocessors. In some embodiments, a computer, a network of computers, and/or portions thereof can be the signal processor.

The term "computer" is intended to have a broad meaning to include any devices that are capable of performing the intended functional steps. For example, mainframe, desktop, laptop, tablet and smart phone devices and any combination or networks thereof, are intended to be included within, but not limited to, the definition of the term "computer". A computer can have one processor, such as a central processing unit (CPU), or a plurality of processors in some embodiments. A computer can have memory, data storage and/or data input and data output devices in some embodiments.

The term "signal" is intended to have a broad meaning to include both digital and analog signals. In one limit, a signal can be a value at a single point in time; however, a signal can also be a time series of discrete and/or continuous values. Waveforms are examples of signals in some embodiments.

The term "machine learning model" is intended to have a broad meaning to include a model developed based software algorithms that can improve performance of the model by one or more training procedures implemented by a computer without the computer having to be explicitly programmed based on the data. For example, neural networks techniques, support vector machine techniques can be used for implementing the machine learning model. However, other embodiments could utilize one or more of the large number of available machine learning algorithms.

The term "subject" refers to a particular person or animal, i.e., an individual, and not a generic, standard or idealized person or individual. In other words, the simulations are personalized.

A computing device may perform certain functions in response to processor executing software instructions contained in a computer-readable medium, such as a memory. In alternative embodiments, hardwired circuitry may be used in place of or in combination with software instructions to implement features consistent with principles of the disclosure. Thus, implementations consistent with principles of the disclosure are not limited to any specific combination of hardware circuitry and software.

Example embodiments may be embodied in many different ways as a software component. For example, it may be a stand-alone software package, a combination of software packages, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application. It may also be embodied as a software package installed on a hardware device such as a CT or MRI scanner, for example.

Some embodiments of the instant disclosure are directed to novel approaches of non-invasively establishing the LVEDP by using: 1) specific hemodynamic relationships; 2) measurement techniques and systems to measure key parameters; and 3) algorithmic approaches to use the measured parameters and hemodynamic relationships to derive the Left Ventricular End Diastolic Pressure (LVEDP).

Some embodiments of the instant invention are directed to a system for non-invasively determining at least one of left ventricular end diastolic pressure (LVEDP) or pulmonary capillary wedge pressure (PCWP) in a subject's heart, comprising: a signal processor; a pressure sensor operatively connected to said signal processor to communicate therewith; and a timing sensor operatively connected to said signal processor to communicate therewith, wherein said pressure sensor is structured to be brought into mechanical connection with an external surface region of said subject so as to provide peripheral pressure signals corresponding to a peripheral artery blood pressure, wherein said timing sensor is structured to non-invasively measure a physical property of said subject's heart that is correlated with said subject's heart beat so as to provide timing signals comprising timing information with respect to heartbeat cycles, and wherein said signal processor is configured to receive said peripheral pressure signals and said timing signals and to non-invasively determine an estimated value of said subject's LVEDP or PCWP based at least partially thereon.

Some embodiments of the instant invention are directed to a system for non-invasively determining at least one of left ventricular end diastolic pressure (LVEDP) or pulmonary capillary wedge pressure (PCWP) in a subject's heart, comprising a timing sensor wherein said timing sensor is at least one of an acoustic sensor capable of providing a phonocardiogram, an electrical sensor capable of providing an electrocardiogram, or optical sensor, or an impedance sensor.

Some embodiments of the instant invention are directed to a system for non-invasively determining at least one of left ventricular end diastolic pressure (LVEDP) or pulmonary capillary wedge pressure (PCWP) in a subject's heart, comprising a blood pressure sensor operatively connected to a signal processor to communicate therewith, wherein said blood pressure sensor is structured to be brought into mechanical connection with an external surface region of said subject so as to provide signals corresponding to diastolic blood pressure of said subject, and wherein said signal processor is further configured to receive said diastolic blood pressure signals and to non-invasively determine an estimated value of said subject's LVEDP or PCWP based at least partially on peripheral pressure signals, timing signals and diastolic blood pressure signals.

Some embodiments of the instant invention are directed to a system for non-invasively determining at least one of left ventricular end diastolic pressure (LVEDP) or pulmonary capillary wedge pressure (PCWP) in a subject's heart, wherein peripheral pressure signals, timing signals and diastolic blood pressure signals are taken at times while said subject is undergoing a heart failure event and at times subsequent to said heart failure event.

Some embodiments of the instant invention are directed to a system for non-invasively determining at least one of left ventricular end diastolic pressure (LVEDP) or pulmonary capillary wedge pressure (PCWP) in a subject's heart, comprising signal processor configured to non-invasively determine an estimated value of said subject's LVEDP or PCWP using a machine learning model.

Some embodiments of the instant invention are directed to a system for non-invasively determining at least one of left ventricular end diastolic pressure (LVEDP) or pulmonary capillary wedge pressure (PCWP) in a subject's heart, comprising a machine learning system wherein said machine learning model is trained on said subject during a heart failure event.

Some embodiments of the instant invention are directed to a system for non-invasively determining at least one of left ventricular end diastolic pressure (LVEDP) or pulmonary capillary wedge pressure (PCWP) in a subject's heart, comprising a machine learning system wherein said machine learning model is a neural network machine learning model.

Some embodiments of the instant invention are directed to a system for non-invasively determining at least one of left ventricular end diastolic pressure (LVEDP) or pulmonary capillary wedge pressure (PCWP) in a subject's heart, comprising a machine learning system wherein said neural network machine learning model is a feed forward neural network that provides at least said estimated LVEDP or PCWP.

Some embodiments of the instant invention are directed to a system for non-invasively determining at least one of left ventricular end diastolic pressure (LVEDP) or pulmonary capillary wedge pressure (PCWP) in a subject's heart, comprising a machine learning system wherein said neural network machine learning model is a recurrent neural network that provides an estimated LVEDP waveform or PCWP.

Some embodiments of the instant invention are directed to a system for non-invasively determining at least one of left ventricular end diastolic pressure (LVEDP) or pulmonary capillary wedge pressure (PCWP) in a subject's heart, comprising a machine learning system wherein said machine learning model is calibrated to said subject comprising: taking peripheral pressure signals and timing signals during a catheterization procedure; measuring a left ventricular end diastolic pressure in said subjects heart during said catheterization procedure; and correlating said peripheral pressure signals and said timing signals to said left ventricular end diastolic pressure. Some embodiments further comprise altering said left ventricular end diastolic pressure in said subject during said catheterization procedure by manipulating fluid status in said subject, performing a Valsalva maneuver on said subject, exposing said subject to an exercise, or a combination thereof.

Some embodiments of the instant invention are directed to a computer-implemented method for non-invasively determining at least one of left ventricular end diastolic pressure (LVEDP) or pulmonary capillary wedge pressure (PCWP) in a subject's heart, comprising: receiving, by a computer, a plurality of signals from a plurality of non-invasive sensors that measure a plurality of physiological effects that are correlated with functioning of said subject's heart, said plurality of physiological effects including at least one signal correlated with left ventricular blood pressure and at least one signal correlated with timing of heartbeat cycles of said subject's heart; training a machine learning model on said computer using said plurality of signals for periods of time in which said plurality of signals were being generated during a heart failure event of said subject's heart; determining said LVEDP or PCWP using said machine learning model at a time subsequent to said training and subsequent to said heart failure event.

Some embodiments of the instant invention are directed to the computer-implemented method for non-invasively determining at least one of left ventricular end diastolic pressure (LVEDP) or pulmonary capillary wedge pressure (PCWP) in a subject's heart above, wherein at least one signal correlated with left ventricular blood pressure corresponds to peripheral artery blood pressure, and wherein said at least one signal correlated with timing of heartbeat cycles of said subject's heart corresponds to at least one of an acoustic signal or an electrical signal.

Some embodiments of the instant invention are directed to the computer-implemented method for non-invasively determining at least one of left ventricular end diastolic pressure (LVEDP) or pulmonary capillary wedge pressure (PCWP) in a subject's heart above, wherein said machine learning model is a neural network machine learning model.

Some embodiments of the instant invention are directed to the computer-implemented method for non-invasively determining at least one of left ventricular end diastolic pressure (LVEDP) or pulmonary capillary wedge pressure (PCWP) in a subject's heart above, wherein said neural network machine learning model is a feed forward neural network that provides at least said estimated LVEDP or said PCWP.

Some embodiments of the instant invention are directed to the computer-implemented method for non-invasively determining at least one of left ventricular end diastolic pressure (LVEDP) or pulmonary capillary wedge pressure (PCWP) in a subject's heart above, wherein said neural network machine learning model is a recurrent neural network that provides an estimated LVEDP waveform or PCWP.

Some embodiments of the instant invention are directed to the computer-implemented method for non-invasively determining at least one of left ventricular end diastolic pressure (LVEDP) or pulmonary capillary wedge pressure (PCWP) in a subject's heart above, wherein said machine learning model is calibrated to said subject comprising: taking said plurality of physiological effects during a catheterization procedure; measuring a left ventricular end diastolic pressure in said subject's heart during said catheterization procedure; and correlating said plurality of physiological effects to said left ventricular end diastolic pressure. Some embodiments further comprise altering said left ventricular end diastolic pressure in said subject during said catheterization procedure by manipulating fluid status in said subject, performing a Valsalva maneuver on said subject, exposing said subject to an exercise, or a combination thereof.

Some embodiments of the instant invention are directed to a computer-readable medium comprising computer-executable code for non-invasively determining at least one of left ventricular end diastolic pressure (LVEDP) or pulmonary capillary wedge pressure (PCWP) in a subject's heart, said computer-readable medium, when executed by said computer causes said computer to: receive a plurality of signals from a plurality of non-invasive sensors that measure a plurality of physiological effects that are correlated with functioning of said subject's heart, said plurality of physiological effects including at least one signal correlated with left ventricular blood pressure and at least one signal correlated with timing of heartbeat cycles of said subject's heart; train a machine learning model on said computer using said plurality of signals for periods of time in which said plurality of signals were being generated during a heart failure event of said subject's heart; determine said LVEDP or PCWP using said machine learning model at a time subsequent to said training and subsequent to said heart failure event.

Some embodiments of the instant invention are directed to the computer-readable medium above wherein said at least one signal correlated with left ventricular blood pressure corresponds to peripheral artery blood pressure, and wherein said at least one signal correlated with timing of heartbeat cycles of said subject's heart corresponds to at least one of an acoustic signal or an electrical signal.

Some embodiments of the instant invention are directed to the computer-readable medium above, wherein said machine learning model is a neural network machine learning model.

Some embodiments of the instant invention are directed to the computer-readable medium above, wherein said neural network machine learning model is a feed forward neural network that provides at least said estimated LVEDP or PCWP.

Some embodiments of the instant invention are directed to the computer-readable medium above, wherein said neural network machine learning model is a recurrent neural network that provides an estimated LVEDP waveform or PCWP.

Some embodiments of the instant invention are directed to the computer-readable medium above, wherein said machine learning model is calibrated to said subject comprising taking said plurality of physiological effects during a catheterization procedure; measuring a left ventricular end diastolic pressure in said subject's heart during said catheterization procedure; and correlating said plurality of physiological effects to said left ventricular end diastolic pressure. Some embodiments further comprise altering said left ventricular end diastolic pressure in said subject during said catheterization procedure by manipulating fluid status in said subject, performing a Valsalva maneuver on said subject, exposing said subject to an exercise, or a combination thereof.

FIG. 1 shows a schematic of an embodiment of the invention. Figure shows a system 100 for non-invasively determining at least one of left ventricular end diastolic pressure (LVEDP) or pulmonary capillary wedge pressure (PCWP) in a subject's heart having: a signal processor 104; a pressure sensor 102 operatively connected to the signal processor to communicate therewith; and a timing sensor 106 operatively connected to the signal processor to communicate therewith, wherein the pressure sensor is structured to be brought into mechanical connection with an external surface region of the subject so as to provide peripheral pressure signals corresponding to a peripheral artery blood pressure, wherein the timing sensor is structured to non-invasively measure a physical property of the subject's heart that is correlated with the subject's heart beat so as to provide timing signals comprising timing information with respect to heartbeat cycles, and wherein the signal processor is configured to receive the peripheral pressure signals and the timing signals and to non-invasively determine an estimated value of the subject's LVEDP or PCWP based at least partially thereon.

Figure 2:
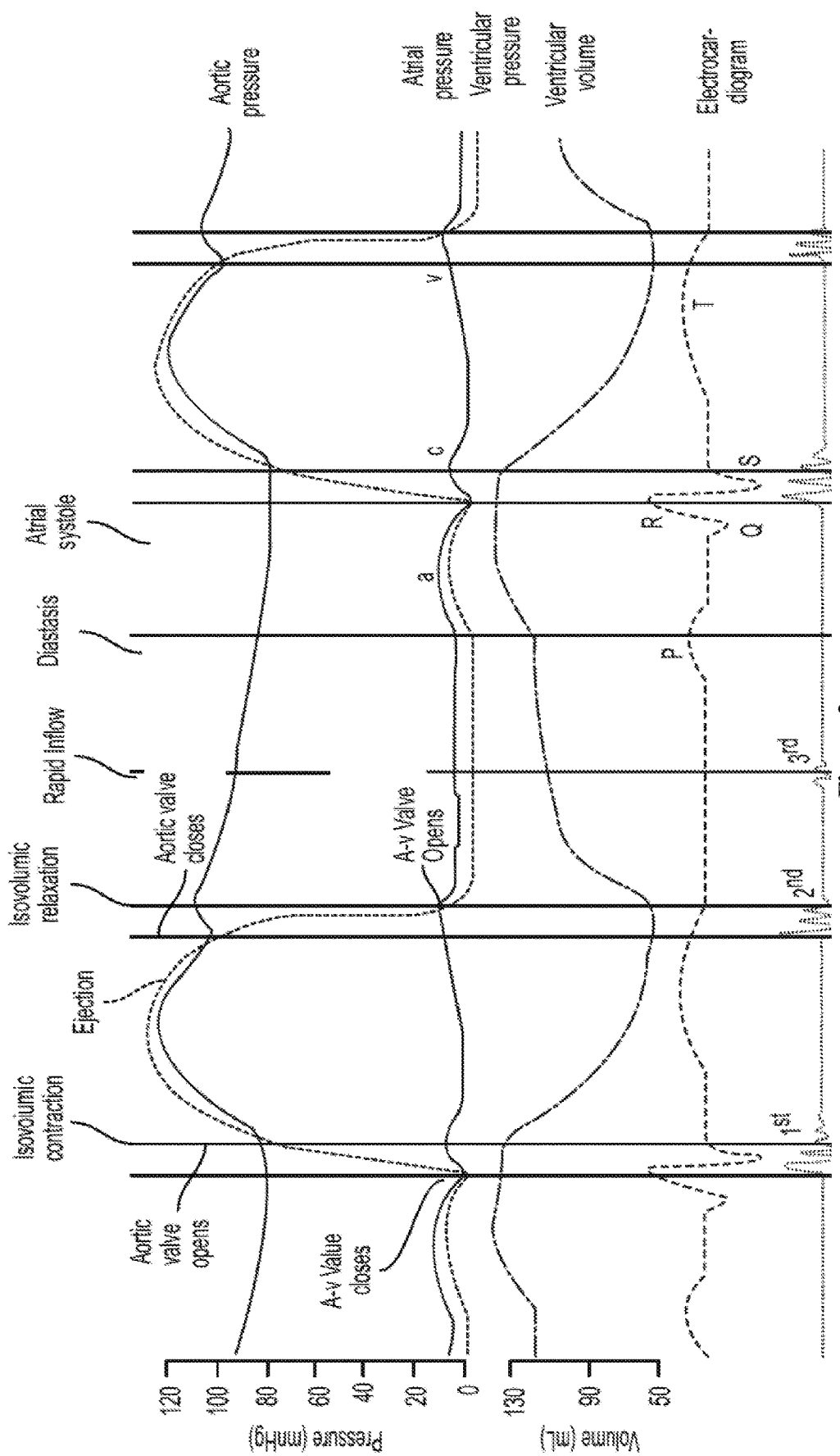
FIG. 2 shows Wigger's diagram.

The physiological and temporal relationships between pressure waves, electronic signals and acoustic signals during the cardiac cycle were used to calculate a patient's LVEDP. This relationship can be accurately illustrated by the Wigger's diagram depicted in FIG. 2.

In some embodiments of the invention, the ventricular pressure waveform is obtained during a cardiac catheterization procedure through the catheter and a cardiologist then determines based on training the patient's LVEDP value. The left ventricle is adjacent both physically and functionally to the aorta and therefore it was found that the pressure waveforms have a relationship that could be learned and reproduced. However, certain patient specific parameters, such as arterial stiffness, influence the specifics of this reproducibility. Therefore, it was found that on a patient to patient basis, a left ventricular waveform, and an LVEDP value could be obtained by manipulating the aortic waveform. The aortic waveform is an arterial waveform that can only be obtained invasively. However, recent studies have shown that there is a quantifiable relationship and a transfer function that could reproduce a central aortic pressure waveform using a peripheral arterial pressure waveform. Therefore, the reproduction of the LVEDP waveform using a peripheral waveform that could be obtained non-invasively using applanation tonometry was studied. Temporal relationships of the waves were modelled using phonocardiography, specifically the S1 and S2 heart sounds. These efforts were validated using retrospective patient data as well as prospective animal experiments.

Some embodiments of the invention disclosed herein include method of obtaining a patient's LVEDP value using noninvasive tools that reflect the patient's hemodynamic relationships along with a personalized algorithm that is tailored to each patient's specific physiology.

Some embodiments of the invention disclosed herein also include non-invasive LVEDP measurement for in-hospital, outpatient and home diagnostic monitoring for patients with various disease states (e.g. heart failure, post cardiotomy, etc) and for use pre, peri and post surgical and therapeutic procedures.

Some embodiments of the invention disclosed herein also include a method of estimating LVEDP using a tonometer to obtain peripheral pressure waveforms, a phonocardiograph instrument to obtain heart sounds, a diastolic blood pressure (DBP) value obtained from a blood pressure cuff and a patient-specific algorithm established during a cardiac catheterization procedure.

In some embodiments, a tonometer is a device for applanation tonometry used to determine the shape of the aortic waveform from the radial artery. More generally, a tonometer as described in the instant application is any device that can measure peripheral pressure waveforms from a variety of arteries.

In some embodiments, a stethoscope is used obtain acoustic sounds, for example heart sounds. In some embodiments, this stethoscope is part of a phonocardiograph instrument that is configured to generate a phonocardiogram. One can imagine other devices that capture acoustic sounds can also be used, such as a microphone.

Some embodiments of the invention described herein also include a device for non-invasively collecting data for the measurement of left ventricular end diastolic pressure (LVEDP) in a subject having: a tonometer; and a stethoscope diaphragm; wherein the tonometer and stethoscope diaphragm are coupled so as to simultaneously collect peripheral pressure waveforms and acoustic information, respectively, in a subject.

Some embodiments of the invention can include the following: 1) A LVEDP derivation algorithm derived through the use of Artificial Neural Network tools (feed forward neural networks and layer recurrent neural networks); 2) the use of a single or multiple non-invasive pressure waveform, a blood pressure cuff measurement and a phonocardiography measurement to derive a value of LVEDP; 3) the use of a single or multiple non-invasive pressure waveform and a respiratory waveform to reproduce a left ventricular pressure waveform; 4) the specific selection of parameters collected from hemodynamic, acoustic and electrophysiological parameters through which the abovementioned algorithm is derived; 5) the personalization of the abovementioned algorithm based on a patient's hemodynamic physiological parameters, medical history and physical parameters through a calibration procedure; 6) the calibration procedure during a catheterization procedure where the patient's hemodynamic parameters are altered in a controlled manner; 7) a combination device of stethoscope diaphragm and tonometer in a 'watch' like embodiment; 8) a carotid tonometer device encased in a 'neck-pillow' form factor; 9) a combination device of carotid tonometer and stethoscope diaphragm in a specific embodiment; and/or 10) a method by which device placement is guided.

Some embodiments of the invention are based on the described and validated physiological and temporal relationships between pressure waves, electronic signals and acoustic signals during the cardiac cycle. This relationship can be accurately illustrated by the Wigger's diagram depicted in FIG. 2. Utilizing the hemodynamic relationships best described using the standard Wigger's diagram, the observations as presented in FIG. 3 were made to be able to estimate LVEDP.

Figure 3:
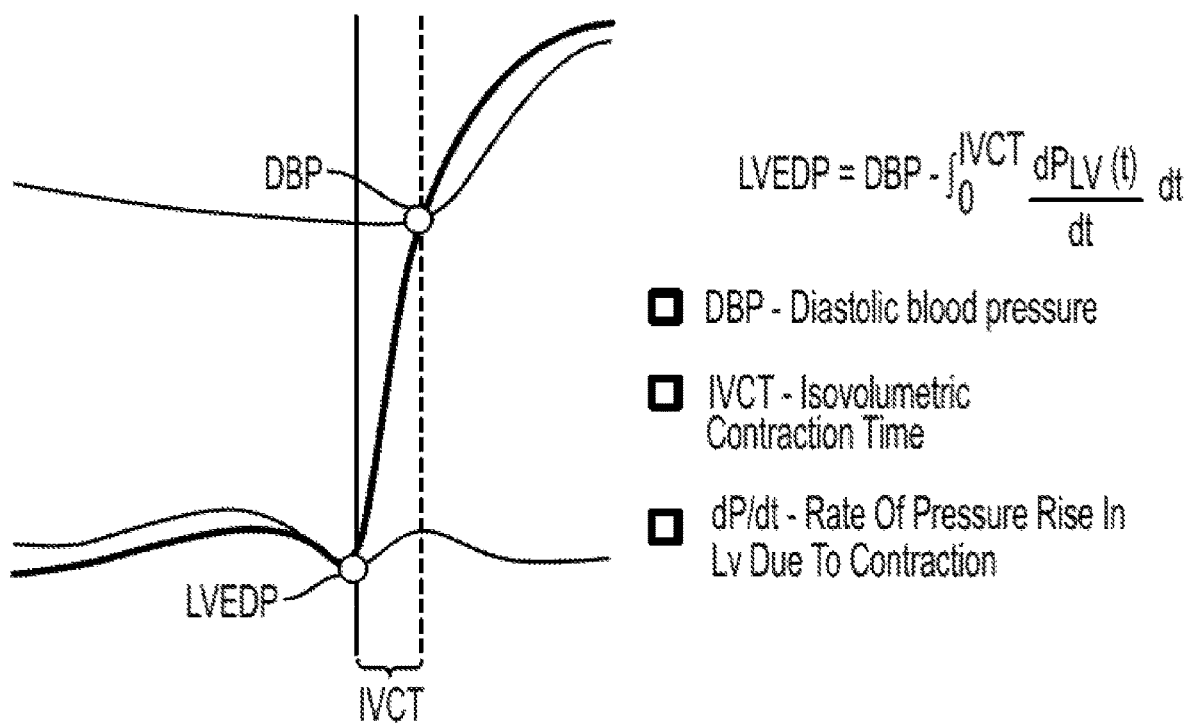
FIG. 3 shows an empirical equation for derivation of LVDEP.

In some embodiments of the invention, the three parameters diastolic blood pressure (DBP), isovolumetric contraction time (IVCT) and rate of pressure rise in LV due to contraction (dp/dT) shown in FIG. 3 are measured in a non-invasive manner to derive the LVEDP. In order to measure these three parameters, some embodiments of the invention employ the following measurement techniques: 1) Peripheral Tonometery to record carotid/radial pressure waveform; 2) Phonocardiography to record 1st and 2nd heart sounds; 3) Blood Pressure Cuff measurement to record diastolic blood pressure; and 4) Calibration against a patient's hemodynamic waveforms during catheterization.

In some embodiments, the methods and systems described herein can be applied to determining LVEDP as well as PCWP. In such embodiments, PCWP is measured using a balloon tipped catheter during a right heart catheterization procedure by wedging the balloon into one of the branches of the Pulmonary artery bed. During diastole when the Mitral valve is open the PCWP=Left Atrial Pressure=Left ventricular end diastolic pressure for most patients. Hence, PCWP is a reasonable surrogate for left heart filling pressures and a frequently used measure clinically as opposed to direct left heart catheter based measurements. The reason for this is that putting catheters into the venous system are related to lower complications than by inserting catheters into the higher pressure arterial system. Further, the access path into the right heart from the Right Internal Jugular vein is usually less tortuous and easily performed by most qualified physician specialties.

The following examples describe some embodiments and some applications in more detail. However, the broad concepts of the current invention are not limited to the particular examples.

EXAMPLES

Example 1—Empirical Equation for Derivation of LVEDP

Utilizing the hemodynamic relationships best described using a standard Wigger's diagram (see FIG. 2), the observations as presented in FIG. 3 were made to be able to estimate LVEDP. FIG. 3 shows a graph and empirical equation (1) for the derivation of LVEDP from various parameters:

$$LVEDP = DBP - \int_0^{IVCT} \frac{dP_{LV}(t)}{dt} dt, \quad (1)$$

where:
LVEDP=Left Ventricular End-Diastolic Pressure
DBP=Diastolic blood pressure;
IVCT=Isovolumetric Contraction time; and
dP/dt=Rate of pressure rise in the Left Ventricle (LV) due to contraction According to equation (1), one measures the 3 parameters DBP, IVCT and dp/dT in a non-invasive manner to derive the LVEDP of a subject. These 3 parameters were measured in the subject via the following measurement techniques: 1) Peripheral Tonometery: to record carotid/radial pressure waveform; 2) Phonocardiography: to record 1st and 2nd heart sounds; 3) Blood Pressure Cuff measurement: to record diastolic blood pressure; and 4) Calibration against the subject's hemodynamic waveforms during catheterization.

In order to make equation (1) more practical, the following discrete equations were used in the algorithm:

$$LVEDP = DBP - IVCT \times \text{ideal} \frac{dP}{dt}, \quad (2)$$

where:
DBP=BP cuff DBP;
Ideal dP/dt =avg $dP_{LV}$/dt=f (periph dP/dt);
IVCT=f(EITC)=f(S1S2-periphEP);
LVEDP=Left Ventricular End-Diastolic Pressure;
DBP=Diastolic Blood Pressure;
dP/dt=Rate of pressure change over time;
IVCT=Internal Isovolumetric Contraction Time;
EICT=External Isovolumetric Contraction Time;
S1S2=Time period between the two heart sounds, S1 and S2; and
EP=Ejection Period, defined as the time between the initial rise of the peripheral pressure waveform (carotid, radial, brachial, etc) to the nadir of the dicrotic notch Both animal studies (in adult pigs) and retrospective analysis of human catheterization data was performed to validate the algorithm. Details of this analysis are discussed below.

In the animal studies, the following instrumentation was used to measure invasive and non-invasive hemodynamic parameters that could later be employed to establish correlation between true measured LVEDP using catheterization and algorithmic predicted values and assess the accuracy of these measurements.

TABLE 1

Tools used to measure various parameters

| Measurement | Tools |
| --- | --- |
| LV waveform | Millar Catheter |
| AO waveform | Millar Catheter |
| S1 and S2 heart sounds | Thinkslabs Electronic Stethoscope |
| Carotid Tonometer | Millar Tonometer (SphygmoCor) |
| ECG | Standard 3-lead ECG |

In order to ensure applicability to a large patient set, LVEDP variations were introduced in the animal using fluid volume or epinephrine injections and the predicated values with these perturbations were compared to measured values.

A similar approach was used to retrospectively analyze previously obtained human data where hemodynamic variations were introduced using Valsalva Maneuvers, Breath-holding, Pacing, Right hand grips, abdominal compressions, dopamine injections, etc.

Figure 4:
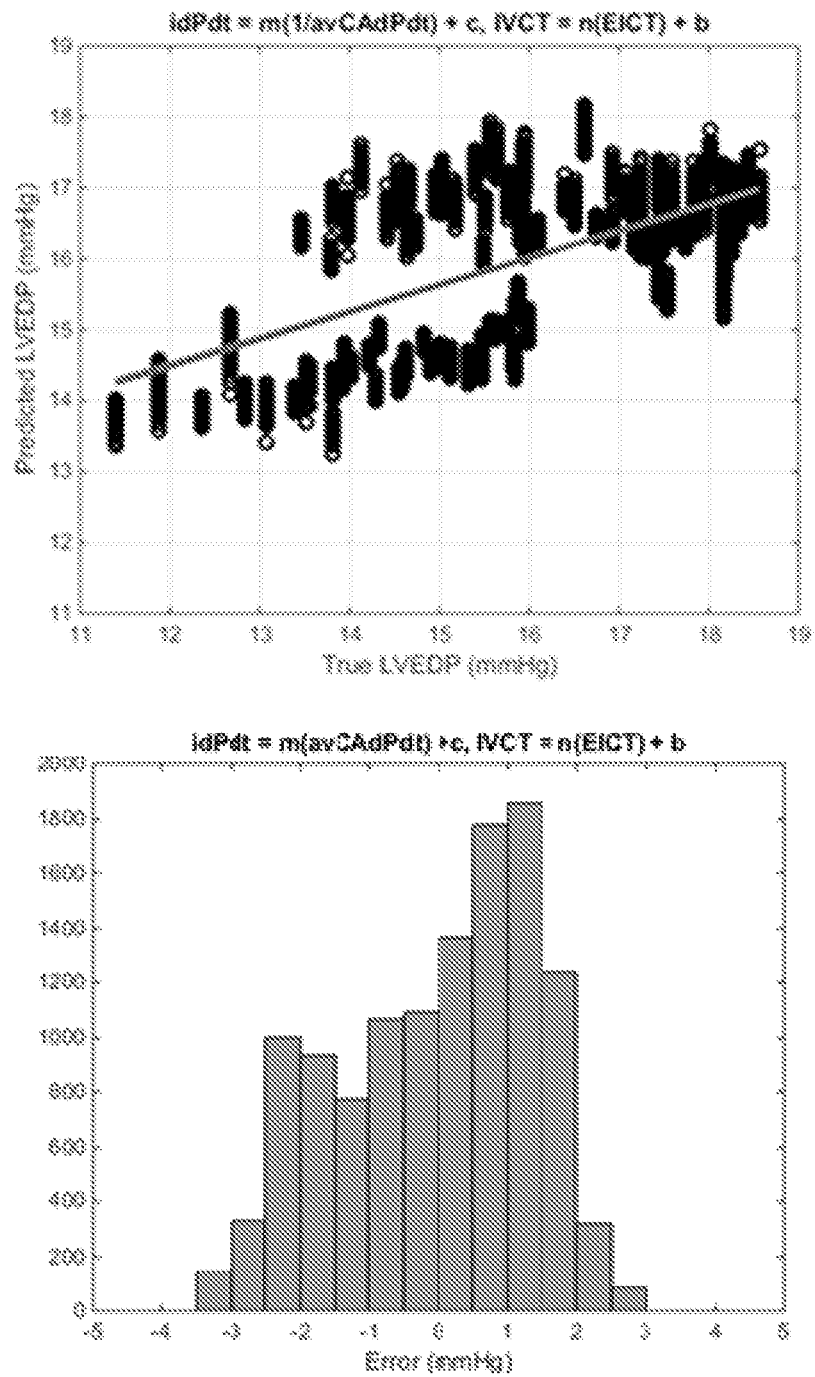
FIG. 4 shows graphs showing the prediction of LVEDP from animal data in the linear regression plot of LVEDP as predicted according to the invention versus true LVEDP obtained from left-heart catheterization (top), and the histogram of the prediction error (bottom)
Figure 5:
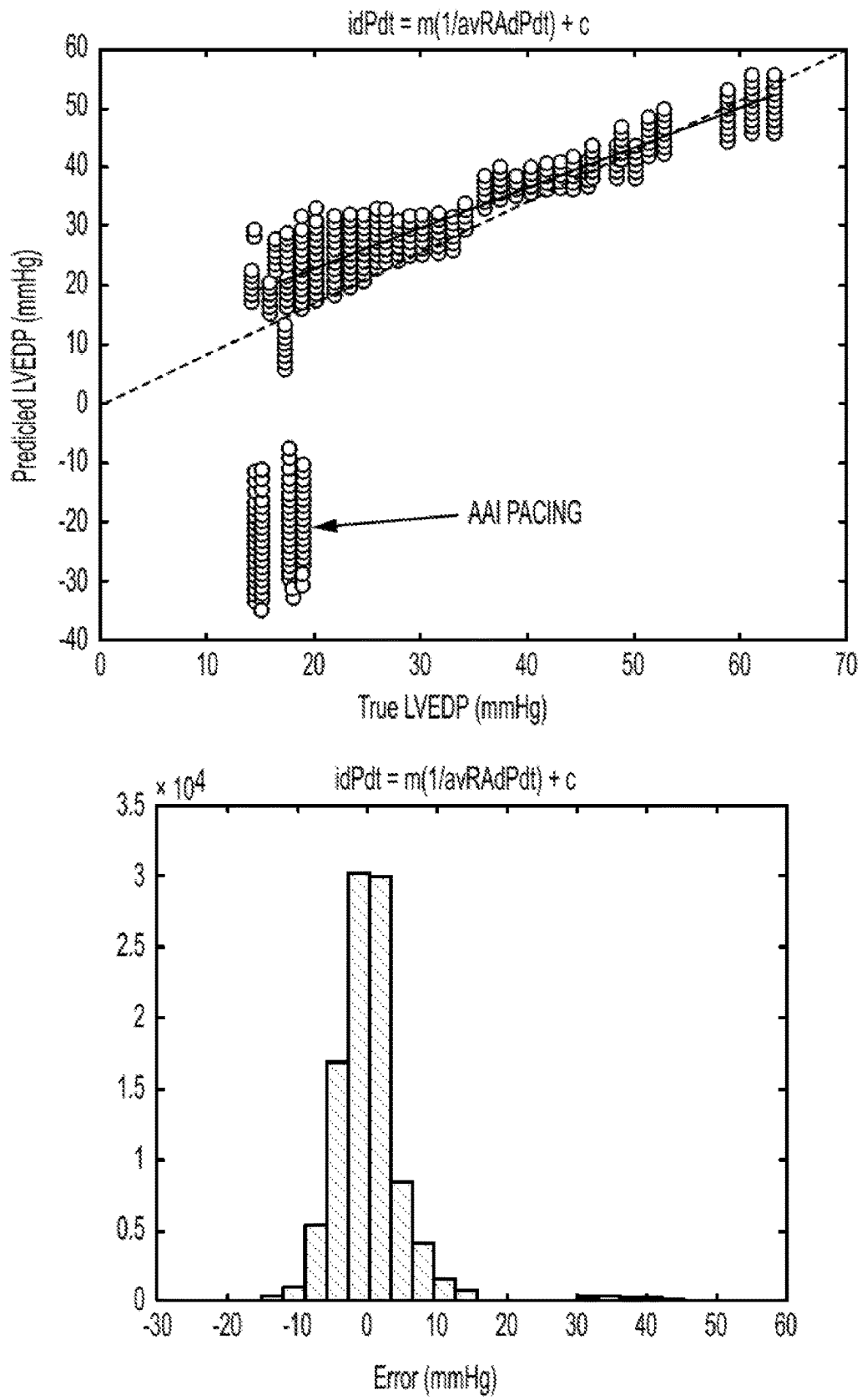
FIG. 5 shows graphs showing the prediction of LVEDP from retrospective human data in the linear regression plot of LVEDP as predicted according to the invention versus true LVEDP obtained from left-heart catheterization (top), and the histogram of the prediction error (bottom)

Details of these analyses are presented in the FIGS. 4 and 5. FIG. 4 is a graph showing the results of the animal studies. FIG. 5 shows the results from the Human data analysis.

In FIG. 4, the prediction of LVEDP from animal data is shown in the linear regression plot LVEDP as predicted according to the invention versus true LVEDP obtained from left-heart catheterization (top), and the histogram of the prediction error (bottom). The predicted LVEDP correlates with the true LVEDP ($R2=0.6$, $p<0.001$) with 98% of the prediction within ±3 mmHg of the true LVEDP. The root mean-square error of the prediction with respect to the true LVEDP is 1.4 mmHg. This prediction accuracy is clinically meaningful according to cardiologists.

In FIG. 5, the prediction of LVEDP from retrospective human data is shown in the linear regression plot LVEDP as predicted according to the invention versus true LVEDP obtained from left-heart catheterization (top), and the histogram of the prediction error (bottom). The predicted LVEDP correlates with the true LVEDP ($R2=0.8$, $p<0.001$) with 61% of the prediction lying within ±3 mmHg of the true LVEDP. The root mean-square error of the prediction with respect to the true LVEDP is 5.5 mmHg. This prediction accuracy is clinically meaningful according to cardiologists.

Example 2—Algorithm Development and Use of Recurrent Neural Network

Figure 6:
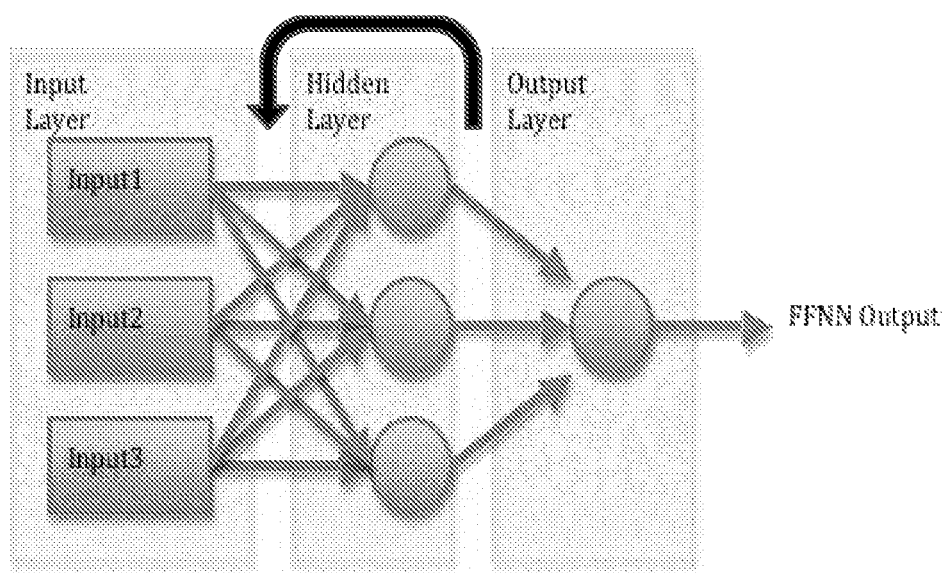
FIG. 6 shows a schematic of a recurrent neural network.

There are various methods and tools through which the relationship between measured hemodynamic parameters and left ventricular end diastolic pressure can be mathematically modeled. For example, Matlab's artificial neural network tools can be used to explore and untangle the intricacies of this relationship, although other artificial neural networks can be used. FIG. 6 shows a schematic of such a recurrent neural network. The first approach was to attempt to train the neural network to reproduce the Left Ventricle (LV) waveform by exposing it to a training data set with a peripheral pressure waveform as the input, and a LV pressure waveform as the target. The network was then validated and then tested on a separate mutually orthogonal set of LV waveforms and the closeness of reproducibility was documented. It was found that the model could accurately and closely reproduce the LV pressure waveform as long as the fluid status of the patient/animal was consistent with levels seen during model training. The model could not be used to replicate the pressure waveforms accurately when it had not been trained with waveforms associated with that fluid level.

A second approach to mathematically model this relationship involved selection of certain permutations of hemodynamic physiological parameters obtained from a patient's non-invasively obtained measurements fed into a Matlab feed forward neural network and trained to reproduce a certain associated value of LVEDP. These parameters were input into the toolbox, and the network was trained to learn the relationship between these values and the corresponding target LVEDP value. The learned network was then tested on another set of parameters and the correlation between true LVEDP and model predicted LVEDP was tracked. The model was found to accurately predict LVEDP values in ranges to which it had been exposed to before (R-square>0.9, $p<0.001$).

Parameters used in the neural network were collected on a cycle to cycle basis or across multiple cycles and these include but were not limited to: diastolic blood pressure, systolic blood pressure, peripheral waveform ejection period, peripheral waveform average change in pressure over time, peripheral waveform maximum change in pressure over time, external isovolumetric contraction time, peripheral pulse pressure (which is defined as difference between diastolic blood pressure and systolic blood pressure), peripheral waveform dicrotic notch pressure, peripheral waveform augmentation index, parameters of arterial stiffness, heart rate, indices of peripheral waveform, the period between first heart sound and key indices on the peripheral waveform, the period between the second heart sound and indices on the peripheral waveform, indices of the electrocardiogram (ECG), the period between indices of the ECG and key indices on the peripheral waveform. Peripheral waveform augmentation index can be defined in two ways: 1) the ratio of the augmentation pressure to pulse pressure; or 2) the ratio of the dicrotic notch pressure to pulse pressure. Parameters of arterial stiffness include but are not limited to: pulse wave velocity, pulse wave transit time, ambulatory arterial stiffness index, augmentation index. Indices of the peripheral waveform include but are not limited to: time and pressure of upstroke of the peripheral waveform, time and pressure of peak of the peripheral waveform, time and pressure of peak or nadir of dicrotic notch of the peripheral waveform, time and pressure of peak or nadir of the augmentation pressure. Indices of the electrocardiogram (ECG) include but are not limited to: R wave, S wave, Q wave, T wave, P wave.

Insights gained from the neural network model could augment equation (1) to obtain a hybrid model leveraging both physiological relationships as well as empirical mathematical relationships to create a more accurate and predictive model.

Both animal studies (in adult pigs) and retrospective analysis of human catheterization data was performed to validate the algorithm. Details of this analysis are presented below.

In order to ensure applicability to a large patient set, LVEDP variations were introduced in the animal using fluid volume or epinephrine injections and the predicated values with these perturbations were compared to measured values.

A similar approach was used to retrospectively analyze previously obtained human data where hemodynamic variations were introduced using Valsalva Maneuvers, Breath-holding, Pacing, Right hand grips, abdominal compressions, dopamine injections, etc.

Details of these analyses are presented in the Figures and discussion below.

Table 2 shows representative examples of model parameter combinations used to measure LVEDP, including Error analysis.

TABLE 2

Representative examples of inputs combinations for 10 patient data.

| Patient | Input Parameters | $R^2$ | Error Analysis | | |
|---|---|---|---|---|---|
| | | | RMSE (mmHg) | Median (mmHg) | Upper 95% CI (mmHg) |
| 01 | DBP, SBP, IVCT, Time$_{DBP-SBP}$, AId, HR, RAu-S2 | 0.95 | 2.09 | 0.13 | 1.55 |
| 02 | DBP, SBP, IVCT, avRAdPdt, HR, RAu-S2 | 0.91 | 2.79 | 0.12 | 2.20 |
| 03 | DBP, SBP, IVCT, pkRAdPdt, AId, HR, RAu-S2 | 0.89 | 2.49 | 0.12 | 1.81 |
| 04 | DBP, SBP, IVCT, Time$_{DBP-SBP}$, AI, HR, RAu-S2 | 0.96 | 2.08 | 0.10 | 1.58 |
| 05 | DBP, SBP, IVCT, Time$_{DBP-SBP}$, AI, HR, RAu-S2 | 0.73 | 2.03 | 0.12 | 1.58 |
| 06 | DBP, SBP, IVCT, Time$_{DBP-SBP}$, AI, HR, RAu-S2 | 0.92 | 1.57 | 0.04 | 1.20 |
| 07 | DBP, SBP, IVCT, AI, HR, RA-S2 | 0.86 | 1.00 | 0.05 | 0.79 |
| 08 | DBP, SBP, IVCT, Time$_{DBP-SBP}$, AI, HR, RAu-S2 | 0.87 | 1.84 | 0.02 | 1.38 |
| 09 | DBP, SBP, IVCT, pkRAdPdt, AI, HR, RAu-S2 | 0.86 | 1.76 | 0.04 | 1.23 |
| 10 | DBP, SBP, IVCT, pkRAdPdt, HR, RAu-S2 | 0.80 | 3.47 | 0.22 | 2.68 |

Abbreviation for Table 2: DBP—Diastolic Blood Pressure, SBP—Systolic Blood Pressure, IVCT—Isovolumic Contraction Time, Time$_{DBP-SBP}$—Time interval between minimum and maximum of peripheral pressure wave, avRAdPdt—Average rate of pressure rise during radial artery pressure upstroke, pkRAdPdt—Maximum rate of pressure rise during radial artery pressure upstroke, AI—Augmentation Index, AId=Augmentation Index calculated using the pressure at the nadir of the dicrotic notch instead of the peak of augmentation pressure, HR—Heart Rate, RAu-S2—Time interval between the rise of radial artery pressure and second heart sound.

Figure 7:
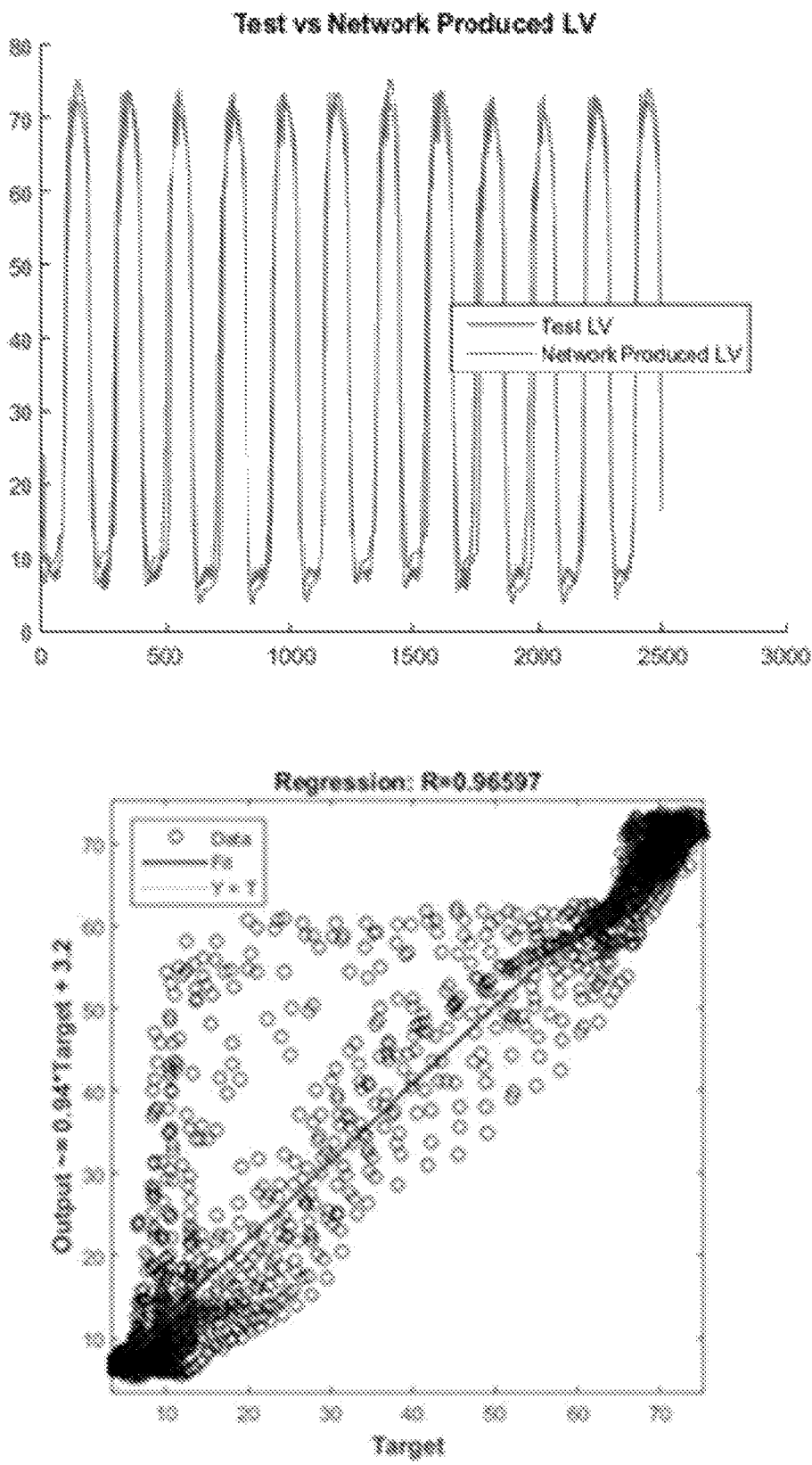
FIG. 7 shows graphs showing the reconstruction of LV pressure waveform from an animal's non-invasively obtained carotid artery (CA) pressure waveform in the plot of the reconstructed LV pressure waveform overlay on top of the true LV pressure waveform obtained from left-heart catheterization (top), and the linear regression plot of reconstructed LV pressure versus true LV pressure.

In FIG. 7, the reconstruction of LV pressure waveform from an animal's non-invasively obtained carotid artery (CA) pressure waveform is shown in the plot of the reconstructed LV pressure waveform overlay on top of the true LV pressure waveform obtained from left-heart catheterization (top), and the linear regression plot of reconstructed LV pressure versus true LV pressure. The reconstructed LV pressure correlates with the true LV pressure (R2=0.9, p<0.001). This result shows that this approach can potentially be used to accurately reconstruct LV pressure waveform from a peripheral pressure waveform, after which, the LVEDP value can be extracted from the reconstructed LV pressure waveform.

Figure 8A:
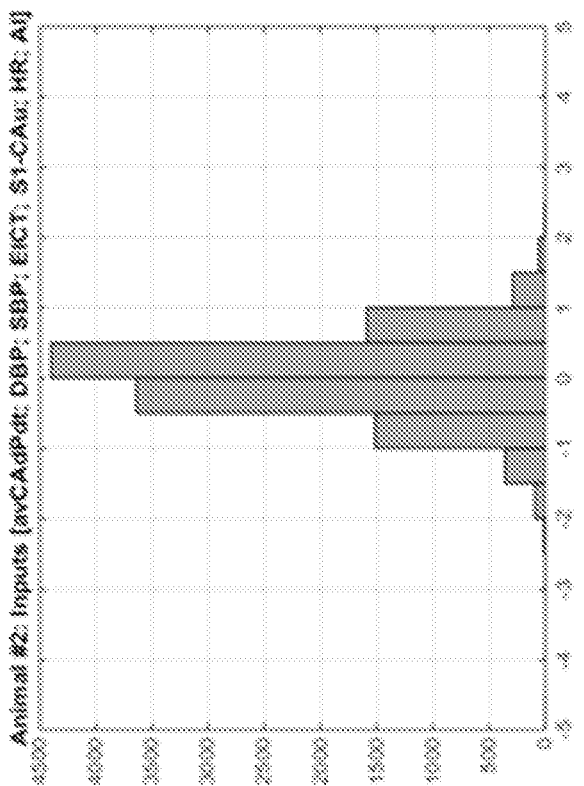
FIGS. 8A and 8B show graphs showing the prediction of LVEDP from animal and human data in the linear regression plot of LVEDP as predicted according to the invention versus true LVEDP obtained from left-heart catheterization, and the histogram of the prediction error.
Figure 8A:
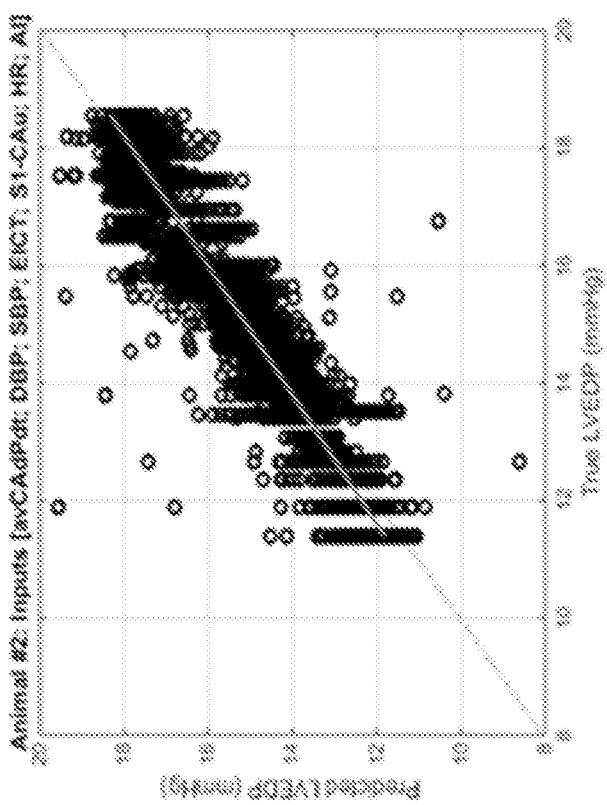
Figure 8B:
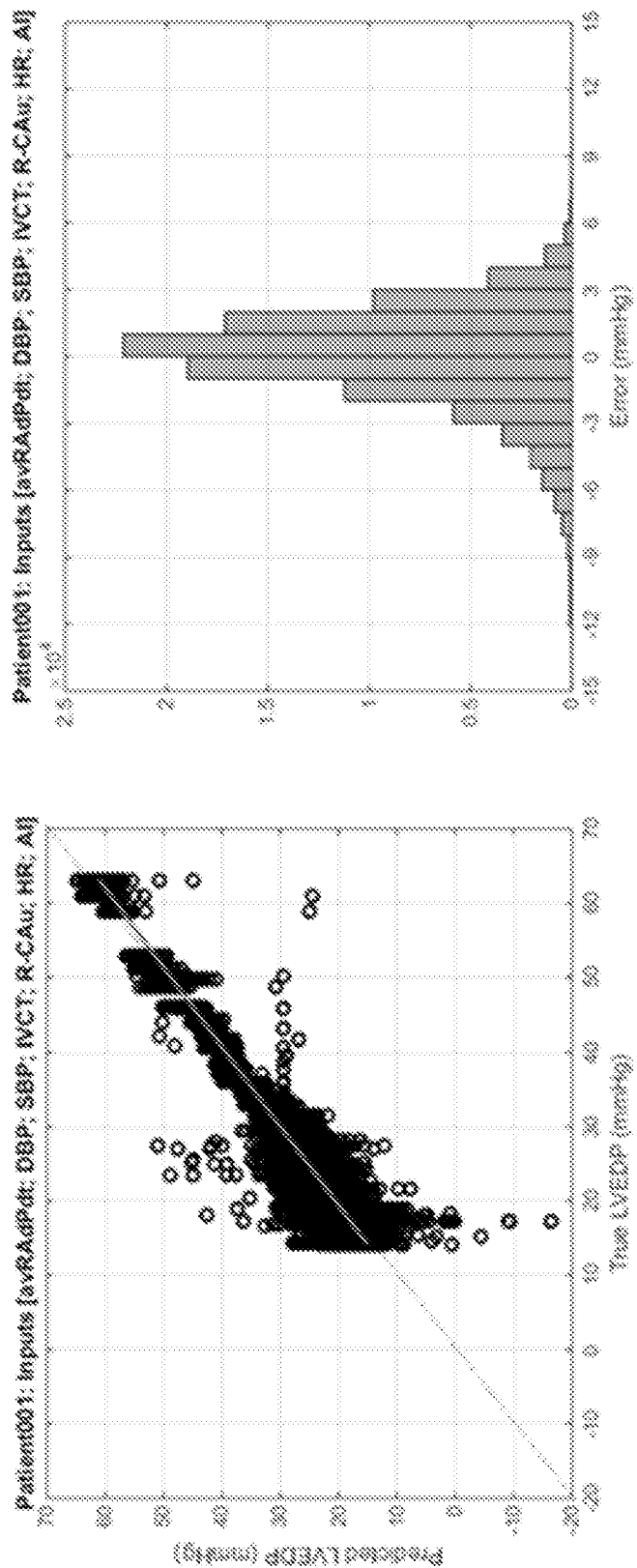

In FIG. 8A, the prediction of LVEDP from animal data is shown in the linear regression plot LVEDP as predicted according to the invention versus true LVEDP obtained from left-heart catheterization (left), and the histogram of the prediction error (right). The predicted LVEDP correlates with the true LVEDP (R2=0.9, p<0.001) with 99% of the prediction within ±3 mmHg of the true LVEDP. The root mean-square error of the prediction with respect to the true LVEDP is 0.6 mmHg. In addition, the prediction of LVEDP from retrospective human data is shown in FIG. 8B in the linear regression plot of LVEDP as predicted according to the invention versus true LVEDP obtained from left-heart catheterization (left), and the histogram of the prediction error (right). The predicted LVEDP correlates with the true LVEDP (R2>0.9, p<0.001) with 85% of the prediction within ±3 mmHg of the true LVEDP. The root mean-square error of the prediction with respect to the true LVEDP is 2.3 mmHg. Both prediction accuracies are clinically meaningful according to cardiologists.

Example 3—Calibration Procedure and Point of Use

Calibration

Figure 9:
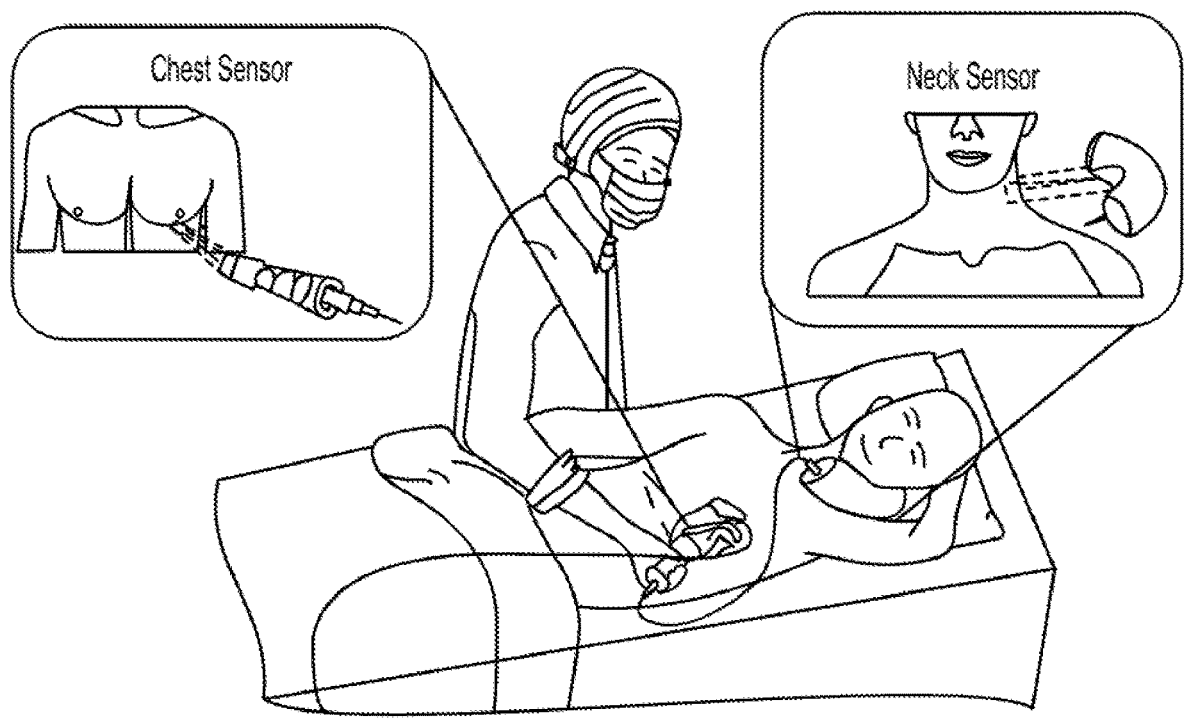
FIG. 9 shows a schematic of device calibration while the subject is in a laying position.

In some device embodiments of the current invention, personalization of the device is an important aspect of the functioning of the device and the technology. Device calibration ensures that the device is specifically applicable to each patient's unique hemodynamic parameters and their relationships. The calibration would be performed during the patient's catheterization procedure. FIG. 9 is an illustration of a procedure for device calibration.

Based on the algorithm development results, it was decided that the calibration procedure for the device and the algorithm would include a controlled manner of altering a patient's LVEDP in a clinically meaningful range. The manners of altering the LVEDP value during calibration include but are not limited to pharmacological manipulation of fluid status, exercise, valsalva maneuver, hand grip exercises etc. When calibrating, peripheral pressure signals and timing signals are taken during the catheterization procedure. At the same time, left ventricular end diastolic pressure in said subject's heart is also measured. The peripheral pressure signals and the timing signals are then correlated to the left ventricular end diastolic pressure.

Point of Use

Some embodiments of the invention are calibrated during a patient's catheterization procedure in comparison to invasive left ventricular and aortic pressure waveforms. Based on the data collected, artificial neural network models are employed to determine the patient specific algorithm through which the non-invasive data collected by the device can be used to produce either a left ventricular waveform or an LVEDP value. The patient would then receive a device, personalized to their own physiology, wherein the algorithm would be loaded into a microprocessing unit. The device would subsequently be able to give a patient's LVEDP value after proper signal acquisition. The device is intended for intermittent use throughout the day as needed. The device could be used by a patient while in a sitting or laying down position. Device placement will be guided using an algorithm built into the device.

Figure 10:
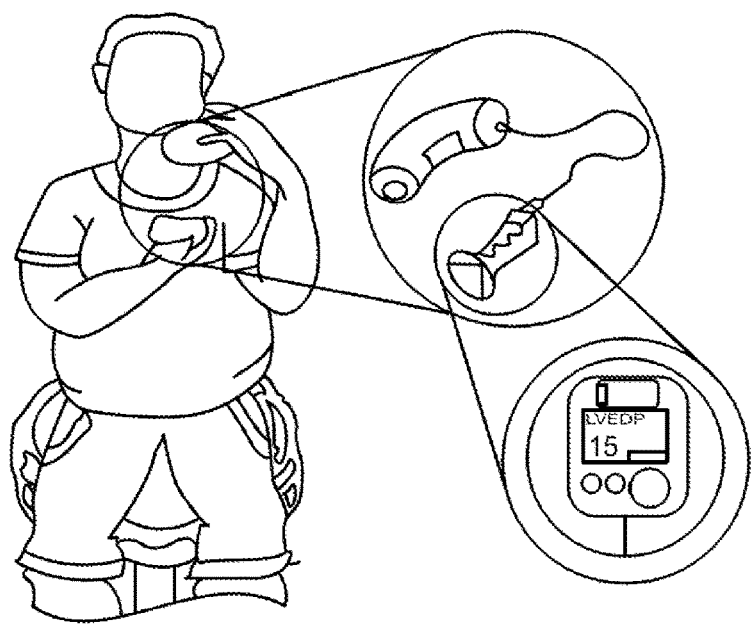
FIG. 10 shows a point of use with an embodiment of the invention.
Figure 13:
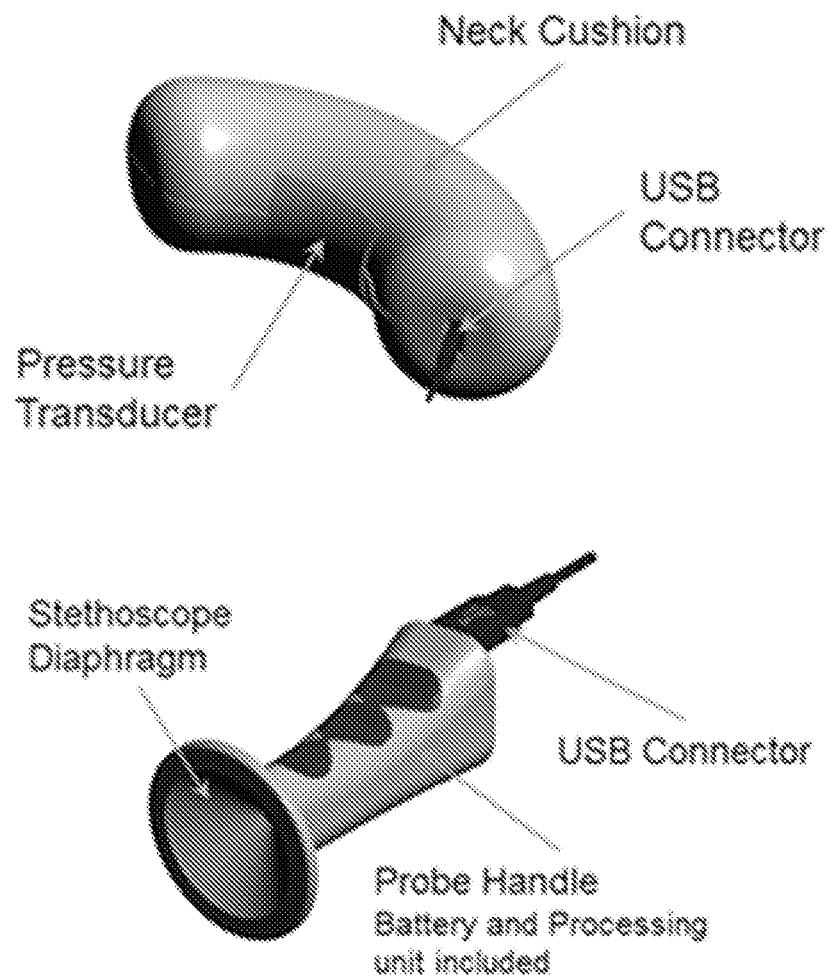
FIG. 13 shows an embodiment of the invention having a carotid tonometer and a phonocardiograph instrument.

FIG. 10 shows an illustration of a point of use wherein the embodiment of the invention is a device comprising a tonometer placed in a neck cushion connected by a USB cable to a stethoscope as in FIG. 13. The stethoscope also contains a display device. The device also contains a microprocessor to analyze the relationship between parameters measured by the tonometer and stethoscope.

Figure 11:
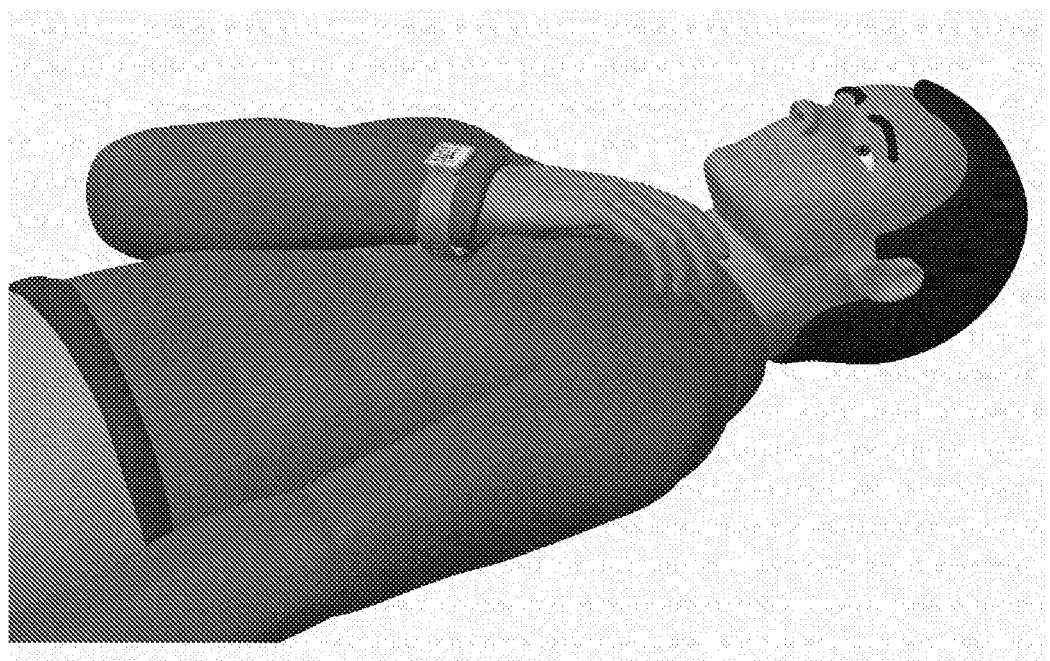
FIG. 11 shows a point of use with an embodiment of the invention, where the subject is in a laying position.
Figure 12:
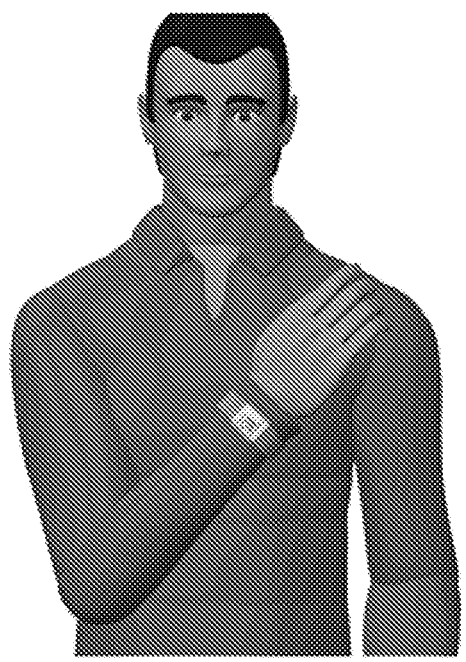
FIG. 12 shows a point of use with an embodiment of the invention, where the subject is in a sitting position.
Figure 14:
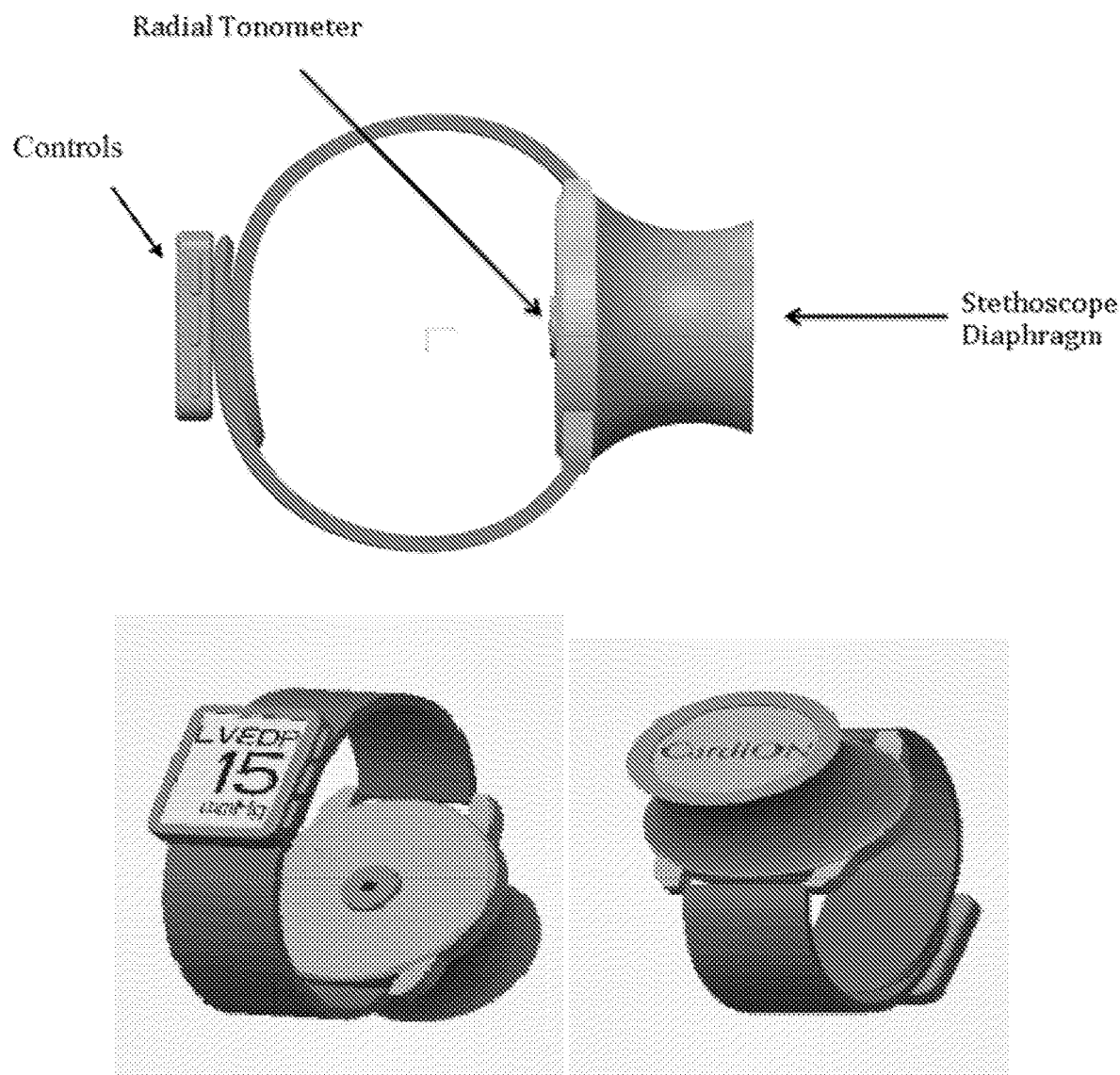
FIG. 14 shows an embodiment of the invention in the form with a radial tonometer.

FIGS. 11 and 12 show illustrations of points of use wherein the embodiment of the invention is a device comprising a tonometer and a stethoscope as in FIG. 14. FIG. 11 shows an illustration of the device being used as a subject is in a laying position. FIG. 12 shows an illustration of the device being used as a subject is in a sitting position.

Example 4—Example Device Embodiments

In the embodiment employing the devices depicted in FIG. 13, carotid tonometry and phonocardiography are used. The carotid tonometer is encased in the form of a neck pillow to ensure proper device placement and comfort. The carotid tonometer (neck sensor/pressure sensor) is connected to the phonocardiograph instrument through a wired USB connection. In this embodiment, a tonometer is used to measure the pressure waveform of the carotid artery. The phonocardiograph instrument is used to obtain heart sounds. The phonocardiograph instrument has a probe handle and a stethoscope diaphragm. A (separate or included) blood pressure cuff is also used.

FIG. 14 shows an alternative device according to some embodiments of the invention. The device of FIG. 14 is a radial tonometer that is worn pressed on a patient's wrist, with a stethoscope diaphragm on the adjacent but opposite side of the device. The controls of the device may be located on the wrist as well. The radial tonometer captures and measures peripheral pressure waveforms. The stethoscope diaphragm is used to obtain heart sounds. In this embodiment, the stethoscope diaphragm is part of a phonocardiograph instrument. In FIG. 14, the device can be in the form of a wristband. This wristband may be a single band attached to the components, or it can be made up of 2 (or more) individual bands that can be connected. One of ordinary skill in the art can imagine a variety of means to "close" or adjust the wristband around the wrist of a subject including buckles, Velcro™, adhesives, etc. A (separate or included) blood pressure cuff is also used.

Figure 15:
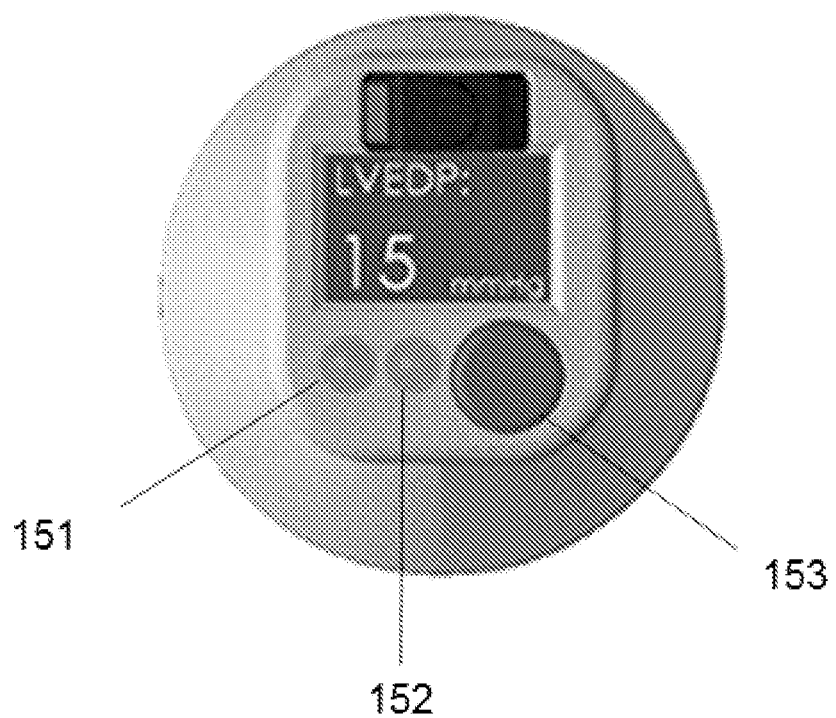
FIG. 15 shows a display device that can be attached to embodiments of the invention.

Embodiments of the invention include algorithms that track and guide placement and proper signal application. Feedback on proper device placement and signal acquisition is given through color-coded LED lights as seen in FIG. 15 (601, 602, 603). A representation of this is shown in black and white in FIG. 15.

Additional embodiments of the invention include configuration of a processor to use a hybrid analysis derived from theoretical and/or physiologically derived and algorithmic models to guide LVEDP measurement.

In addition, other embodiments are configured to use radio waves (such as Bluetooth or Wifi) or other connected ways to transmit data to a terminal and then to the physicians/nurse clinic responsible for the patient. Such embodiments could also include a way for the physician to set thresholds such that deviations from these thresholds could be flagged and highlighted to the physician.

Additional embodiments can also generate diagnoses for the patient guiding treatment using threshold values set by a physician, in addition to allow monitoring once significant clinical usage data and patterns has been established. The embodiment may directly guide the patient to alter their medication without the need for input from a physician based on the LVEDP measurement and the patient could then visit the physician once in 6 months or so.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Martin, C. E. et al, "Direct Correlation of External Systolic Time Intervals with Internal Indices of Left Ventricular Function in Man." Circulation. 1971; 44: 419-431.
2. Chen, C.-H. et al. Estimation of Central Aortic Pressure Waveform by Mathematical Transformation of Radial Tonometry Pressure Validation of Generalized Transfer Function. *Circulation* 95, 1827-1836 (1997).
3. Kips, J. G. et al. Comparison of central pressure estimates obtained from SphygmoCor, Omron HEM-9000AI and carotid applanation tonometry. *J. Hypertens.* 29, 1115-1120 (2011).

We claim:

1. A system for non-invasively determining at least one of left ventricular end diastolic pressure (LVEDP) or pulmonary capillary wedge pressure (PCWP) in a subject's heart, comprising:
   a signal processor;
   a pressure sensor operatively connected to said signal processor to communicate therewith; and
   a timing sensor operatively connected to said signal processor to communicate therewith,
   wherein said pressure sensor is structured to be brought into mechanical connection with an external surface region of said subject so as to provide peripheral pressure signals corresponding to a peripheral artery blood pressure,
   wherein said timing sensor is structured to non-invasively measure a physical property of said subject's heart that is correlated with said subject's heart beat so as to provide timing signals comprising timing information with respect to heartbeat cycles, and wherein said signal processor is configured to receive said peripheral pressure signals and said timing signals and to non-invasively determine an estimated value of at least one of said subject's LVEDP or PCWP based at least partially thereon using a machine learning model that is trained on said subject during a heart failure event.

2. The system according to claim 1, wherein said timing sensor is at least one of an acoustic sensor capable of providing a phonocardiogram, an electrical sensor capable of providing an electrocardiogram, or optical sensor, or an impedance sensor.

3. The system according to claim 2, further comprising a blood pressure sensor operatively connected to said signal processor to communicate therewith, wherein said blood pressure sensor is structured to be brought into mechanical connection with an external surface region of said subject so as to provide signals corresponding to diastolic blood pressure of said subject, and wherein said signal processor is further configured to receive said diastolic blood pressure signals and to non-invasively determine an estimated value of said subject's LVEDP based at least partially on said peripheral pressure signals, said timing signals and said diastolic blood pressure signals.

4. The system according to claim 3, wherein said peripheral pressure signals, said timing signals and said diastolic blood pressure signals are taken at times while said subject is undergoing a heart failure event and at times subsequent to said heart failure event.

5. The system according to claim 1, wherein said machine learning model is a neural network machine learning model.

6. The system according to claim 5, wherein said neural network machine learning model is a feed forward neural network that provides at least said estimated at least one of LVEDP or PCWP.

7. The system according to claim 5, wherein said neural network machine learning model is a recurrent neural network that provides at least one of an estimated LVEDP waveform or PCWP.

8. The system according to claim 1, wherein said machine learning model is calibrated to said subject comprising:

taking said peripheral pressure signals and said timing signals during a catheterization procedure;

measuring a left ventricular end diastolic pressure in said subject's heart during said catheterization procedure; and correlating said peripheral pressure signals and said timing signals to said left ventricular end diastolic pressure.

9. The system according to claim 8, further comprising altering said left ventricular end diastolic pressure in said subject during said catheterization procedure by manipulating fluid status in said subject, performing a Valsalva maneuver on said subject, exposing said subject to an exercise, or a combination thereof.

10. A computer-implemented method for non-invasively determining at least one of left ventricular end diastolic pressure (LVEDP) or pulmonary capillary wedge pressure (PCWP) in a subject's heart, comprising:

receiving, by a computer, a plurality of signals from a plurality of non-invasive sensors that measure a plurality of physiological effects that are correlated with functioning of said subject's heart, said plurality of physiological effects including at least one signal correlated with left ventricular blood pressure and at least one signal correlated with timing of heartbeat cycles of said subject's heart;

training a machine learning model on said computer using said plurality of signals for periods of time in which said plurality of signals were being generated during a heart failure event of said subject's heart;

determining said at least one of LVEDP or PCWP using said machine learning model at a time subsequent to said training and subsequent to said heart failure event.

11. The method of claim 10, wherein said at least one signal correlated with left ventricular blood pressure corresponds to peripheral artery blood pressure, and wherein said at least one signal correlated with timing of heartbeat cycles of said subject's heart corresponds to at least one of an acoustic signal or an electrical signal.

12. The method according to claim 10, wherein said machine learning model is a neural network machine learning model.

13. The method according to claim 12, wherein said neural network machine learning model is a feed forward neural network that provides at least one of said estimated LVEDP or said PCWP.

14. The method according to claim 12, wherein said neural network machine learning model is a recurrent neural network that provides at least one of an estimated LVEDP waveform or PCWP.

15. The method according to claim 10, wherein said machine learning model is calibrated to said subject comprising:

taking said plurality of physiological effects during a catheterization procedure;

measuring a left ventricular end diastolic pressure in said subject's heart during said catheterization procedure; and correlating said plurality of physiological effects to said left ventricular end diastolic pressure.

16. The method according to claim 15, further comprising altering said left ventricular end diastolic pressure in said subject during said catheterization procedure by manipulating fluid status in said subject, performing a Valsalva maneuver on said subject, exposing said subject to an exercise, or a combination thereof.

17. A computer-readable medium comprising non-transitory computer-executable code for non-invasively determining at least one of left ventricular end diastolic pressure (LVEDP) or pulmonary capillary wedge pressure (PCWP) in a subject's heart, said computer-readable medium, when executed by said computer causes said computer to:

receive a plurality of signals from a plurality of non-invasive sensors that measure a plurality of physiological effects that are correlated with functioning of said subject's heart, said plurality of physiological effects including at least one signal correlated with left ventricular blood pressure and at least one signal correlated with timing of heartbeat cycles of said subject's heart;

train a machine learning model on said computer using said plurality of signals for periods of time in which said plurality of signals were being generated during a heart failure event of said subject's heart;

determine said at least one of LVEDP or PCWP using said machine learning model at a time subsequent to said training and subsequent to said heart failure event.

18. The non-transitory computer-readable medium of claim 17, wherein said at least one signal correlated with left ventricular blood pressure corresponds to peripheral artery blood pressure, and wherein said at least one signal correlated with timing of heartbeat cycles of said subject's heart corresponds to at least one of an acoustic signal or an electrical signal.

19. The non-transitory computer-readable medium according to claim 17, wherein said machine learning model is a neural network machine learning model.

20. The non-transitory computer-readable medium according to claim 19, wherein said neural network machine learning model is a feed forward neural network that provides at least one of said estimated LVEDP or PCWP.

21. The non-transitory computer-readable medium according to claim 19, wherein said neural network machine learning model is a recurrent neural network that provides at least one of an estimated LVEDP waveform or PCWP.

22. The non-transitory computer-readable medium according to claim 19, wherein said machine learning model is calibrated to said subject comprising:

taking said plurality of physiological effects during a catheterization procedure;

measuring a left ventricular end diastolic pressure in said subject's heart during said catheterization procedure; and correlating said plurality of physiological effects to said left ventricular end diastolic pressure.

23. The non-transitory computer-readable medium according to claim 22, further comprising altering said left ventricular end diastolic pressure in said subject during said catheterization procedure by manipulating fluid status in said subject, performing a Valsalva maneuver on said subject, exposing said subject to an exercise, or a combination thereof.

* * * * *